United States Patent [19]

Mia

[11] 4,116,633

[45] Sep. 26, 1978

[54] GLOBULIN TEST

[75] Inventor: Abdus Salam Mia, Fairless Hills, Pa.

[73] Assignee: Pitman-Moore, Inc., Washington Crossing, N.J.

[21] Appl. No.: 826,498

[22] Filed: Aug. 22, 1977

[51] Int. Cl.² ............................................. G01N 33/16
[52] U.S. Cl. ................................... 23/230 B; 252/408
[58] Field of Search ....................... 23/230 B; 252/408

[56] References Cited

U.S. PATENT DOCUMENTS

| | | | |
|---|---|---|---|
| 3,607,081 | 9/1971 | Goldenberg | 23/230 B |
| 3,627,468 | 12/1971 | Goldenberg | 23/230 B |

Primary Examiner—R.E. Serwin

[57] ABSTRACT

A reagent for the determination of globulin in serum comprising a solution of ethyl acetate, acetic acid, a ferric salt, sulfuric acid and water. Methods for its preparation and use are disclosed.

9 Claims, No Drawings

GLOBULIN TEST

BACKGROUND OF THE INVENTION

1. Field of the Invention:

The invention is directed to a composition and a method for the determination of serum globulin.

2. Description of the Prior Art:

Globulins are simple proteins, present in blood, lymph and the cytoplasm of cells. They are usually associated with albumins, one or the other being predominant. They give all the ordinary protein tests and are coagulable by heat.

Globulins differ from the albumins, in that they are insoluble in pure (salt-free) water. However, they are soluble in neutral solutions of the salts of strong acids with strong bases, such as sodium chloride. Globulins require a certain concentration of salt in order to remain in solution. They precipitate when the concentration of salt is lowered by dilution of dialysis. In general the globulins are precipitated by half saturation of their solutions with ammonium sulfate, i.e., by the addition to their solutions of an equal volume of saturated ammonium sulfate solutions. Most globulins are also precipitated from their solutions by saturation with solid sodium chloride or magnesium sulfate.

Blood serum contains a variety of globulins characterized by differences in solubility, in precipitability by ammonium or sodium sulfate, and the in rate of electrophoretic migration.

Colorimetry and photometry have been widely applied in the field of clinical chemistry for the determination of albumin and globulin components in serum and plasma and the diagnosis of disease states. Not all proteins contain the same amino acids, and for this reason color tests give reactions varying in intensity according to the nature and the amount of the groups contained in the particular protein under examination.

One of the oldest tests known for the determination of serum proteins is the so-called biuret test. This test is given by those substances whose molecules contain two carbamyl groups joined either directly together or through a single atom of nitrogen or carbon. The test derives its name from the fact that biuret, which is formed on heating urea to 180° C., responds to the test. Proteins respond positively because their molecules include pairs of aminocarboxyl groups.

Since the biuret reaction determines total serum protein, the albumin and globulin fractions may be determined indirectly by salt fraction or by electrophoresis. In salt fractionation, globulin is precipitated by adding salt solution leaving albumin in solution. The protein concentrations of the unfractionated sample and of the albumin solution are determined by the biuret reaction and the globulin concentration is calculated from the difference of the two. In the electrophoretic method, serum protein is separated into different fractions using starch, gel, agrigel, paper or cellulose acetate electrophoresis. The fractions are strained and their relative proportions are determined. The concentration of different fractions may be determined from these relative proportions and the total protein concentration of the sample determined by biuret reaction. Neither of the above-mentioned methods is entirely satisfactory for routine clinical purposes since both require multiple manipulations.

Albumin and globulin may also be assayed by colorimetric determination of albumin through selective dye-binding with 2-(4'-hydroxyazobenzene)benzoic acid (HABA), bromcresol green or methyl orange and calculating globulin by the difference from total protein. The selective dye-binding method is subject to numerous interference in specie variations, and determinations made by this method are subject to many innacuracies.

Globulin may be directly determined by the well known Hopkins-Cole reaction which is a colorimetric method dependent upon the presence of the tryptophane group in the protein. The tryptophane residue reacts with glyoxalic acid and concentrated sulfuric acid to give a purple color.

Goldenberg (U.S. Pat. No. 3,607,081) developed a reagent for the determination of globulins in biological fluid comprising a solution of glyoxalic acid and cupric sulfate pentahydrate in a mixture of glacial acetic and sulfuric acids. One of the disadvantages of the Goldenberg composition is its requirement for extremely high quantities of the acetic acid component, i.e., from about 80 to about 99 parts per volume.

Neeley et al (Clin. Biochem. 8, pp. 273-278, 1975) developed another reagent for the same purpose which contains glyoxalic acid, copper sulfate, concentrated sulfuric acid and lactic acid. As in the case of Goldenberg composition, the Neeley et al reagent is based on the Hopkins-Cole reaction.

A singular disadvantage of the Goldenberg and the Neeley et al compositions is that both reagents develop considerable interfering color in the presence of albumin. Note Example VI, below.

In U.S. Pat. No. 3,558,516, Wybenga discloses a reagent for the determination of cholesterol in biological fluids which comprises ferric perchlorate in ethyl acetate and sulfuric acid. Similarly, in U.S. Pat. No. 3,001,950 Hopper discloses a mixture of sulfuric acid, acetic anhydride and acetic acid for the same purpose.

The present invention differs from the Wybenga composition in that it contains a critically minimal volume of water. The presence of water is essential for the reaction with globulin to take place, and when present in sufficient quantity, it will completely prevent reaction of cholesterol with the reagent. This is especially true when the added volume of water is at least 15% v/v concentration. Example VIII below shows the non-reactivity of the novel composition with cholesterol and the identity of results obtained against sera with and without added cholesterol.

In general, none of the prior art procedures has been entirely satisfactory. It would be desirable to develop a stable reagent for globulin determination which would contain lower proportions of acid and would produce little or no interfering color when reacted in the presence of albumin. It would also be desirable to develop a method which would give results comparable to that of electrophoretic analyses or salt precipitation in serum of different species.

SUMMARY OF THE INVENTION

This invention is directed to a novel reagent for the determination of globulins in serum and to a method of using the same.

The novel composition is stable, colorless and encounters little or no interference with albumin which constitutes approximately 50% of serum proteins.

The novel reagent for use in the determination of globulins in accordance with the present invention comprises ethyl acetate, sulfuric acid, a ferric salt and glacial acetic acid in water solution. In particular, the novel reagent comprises a photometrically reactive quantity of ethyl acetate and a catalytic quantity of ferric ion, in a mixture of glacial acetic acid, sulfuric acid and water.

The ethyl acetate component of the novel composition may be present in from 10% to 50% v/v but a concentration of about 20% v/v is preferred. The sulfuric acid component may be present in an amount from about 5% to about 40% v/v but a concentration of about 12% v/v is preferred. The glacial acetic acid component may be present in an amount from about 20% to about 70% v/v but a concentration of about 32% v/v is preferred.

The ferric ion may be present in catalytic amounts, and may be incorporated in the solution in a suitable watersoluble salt form as for example, ferric perchlorate, which is the preferred salt, ferric chloride, ferric sulfate, ferric nitrate or any one of a number of other salts. The salt should be present in a quantity from about 0.01 to about 0.04%, preferably about 0.024% w/v.

As described above, the final composition should contain distilled or deionized water in an amount from about at least 15% to about 50% v/v, but a concentration of about 36% is preferred.

For the determination of globulin in serum, the sample containing globulin is mixed with the reagent in a proportion of one volume of sample and from about 20 to about 200 volumes of reagent, the preferred proportion being one volume of sample to 50 volumes of reagent. The mixture of the sample and reagent is held at a temperature of about 85° C. for a period of five minutes to 25 minutes, the preferred temperature and time being about 95° C. for about five minutes.

On heating the mixture for a sufficient period, a purple color complex is formed. The intensity of the color complex is proportional to the concentration of globulin in the sample, and can be measured in a colorimeter or spectrophotometer. The absorbance, which is a measure of the intensity of the color, is determined in the spectrophotometer at a wavelength of 500 millimicrons to 580 millimicrons, the preferred wavelength being 540 millimicrons. A green filter of similar wavelength is used in the colorimeter. The absorbance reading is converted to the concentration by comparing it with a previously constructed calibration curve or to the absorbance of a standard sample with known globulin concentration treated under similar conditions. In order to have results comparable to electrophoretic analysis, a pooled normal serum with globulin concentration determined by electrophoresis should be used as standard or for constructing the calibration curve.

The above-mentioned purple color complex is a reaction product of globulin with ethyl acetate and sulfuric acid, in the presence of ferric ion. The inclusion of water in sufficient volume prevents the production of color with cholesterol. Acetic acid is included to solubilize the protein and to reduce the concentration of the stronger (sulfuric) acid which would otherwise be needed.

DESCRIPTION OF THE PREFERRED EMBODIMENTS

The following examples illustrate the present invention but are not to be construed as limiting the same:

EXAMPLE I

Globulin reagent is prepared as follows:
a. 120 milliliters of concentrated sulfuric acid are slowly added to 320 milliliters of glacial acetic acid with stirring and cooling, taking care that the temperature of the mixture does not exceed 45° C. The mixture is cooled to about 5° C. and 200 milliliters of ethyl acetate are added with similar precaution. 240 Milligrams of ferric perchlorate are separately dissolved in 360 milliliters of distilled water and cooled. To make the reagent for the determination of globulin, the ethyl acetate, sulfuric acid and acetic acid mixture is slowly added to the ferric perchlorate solution with stirring and cooling to from about 5° C. to about 15° C.

b. In an alternative procedure, the reagent is prepared by dissolving 100 Milligrams of ferric perchlorate in 400 milliliters of ethyl acetate, to which 100 milliliters of concentrated sulfuric acid are added with cooling to about 5° C. and stirring, followed by the addition of 200 milliliters of glacial acetic acid. The resultant mixture is cooled to from about 5° C. to about 15° C. and added slowly with stirring and cooling to 300 milliliters of distilled water.

c. In another procedure, 450 milligrams of ferric perchlorate are dissolved in 400 milligrams of distilled water, to which 200 milliliters of concentrated sulfuric acid are added with stirring and cooling to about 5° C. followed by the addition of 200 milliliters of ethyl acetate and 200 milliliters of glacial acetic acid.

d. In still another procedure, a reagent composition is prepared by dissolving 200 milligrams of ferric chloride in 360 milliliters of distilled water, adding 120 milliliters of concentrated sulfuric acid with stirring and cooling to about 5° C, followed by the addition of 300 milliliters of ethyl acetate. The volume is brought to 1000 milliliters by adding glacial acetic acid.

Although any of the above-mentioned formulations may be used for globulin determination, the formulation described in (a) is the preferred embodiment.

EXAMPLE II

Globulin concentration is serum is determined as follows, using the reagent described in Example I (a):

2.5 Milliliters of globulin reagent are added to two tubes labeled blank and test. 50 Microliters of serum sample to be analyzed are added to the tube labeled test, and the contents of the tube are mixed thoroughly. Both tubes are incubated for five minutes at 95° C. to produce a purple color complex in the test sample. After five minutes incubation, the tubes are cooled in cold tap water bath for five minutes.

The absorbance of the test is read against the blank in the spectrophotometer at 540 nm. wavelength. The absorbance reading of the test is converted to concentration (grams of globulin per 100 milliliters of serum) from a previously prepared calibration curve.

The calibration curve is prepared by using a pooled serum sample of human origin (calibration serum), the globulin concentration of which is determined by known electrophoretic methods. The concentration of the test may also be determined from the following formula when the calibration serum is run simultaneously with the unknown serum sample to be analyzed:

Concentration of the test =

$$\frac{\text{Absorbance of test}}{\text{Absorbance of the calibration serum}} \times \text{Concentration of the calibration serum}$$

Globulin concentrations of serum samples from 20 individual animals of each of the following species were determined by the process described above with the following results:

| Animals | Globulin Concentration in Gms./100 ml. Range |
|---|---|
| Canine | 2.5 – 4.5 |
| Feline | 2.4 – 4.0 |
| Equine | 3.8 – 5.4 |
| Bovine | 2.8 – 4.8 |
| Ovine | 2.2 – 4.6 |
| Porcine | 2.3 – 3.9 |

EXAMPLE III

In order to determine the reproducibility of the test, the globulin concentration of a pooled serum sample was determined in 20 replicates. The coefficient of variation of the test was 2.1% with a mean concentration of 2.8 gm. percent.

EXAMPLE IV

The globulin concentration of a series of serum samples was determined simultaneously by the method heretofore described, by the method described by Goldenberg et al, and that described by Neeley et al, for comparison. The results are shown below:

| Samples | Globulin Concentration gm. percent | | |
|---|---|---|---|
| | Present Method | Method of Goldenberg | Method of Neeley |
| 1 | 3.9 | 3.6 | 3.6 |
| 2 | 4.3 | 4.5 | 3.8 |
| 3 | 4.9 | 4.7 | 4.7 |

EXAMPLE V

Serum samples from animals of different species were analyzed for globulin by the method of this invention and by electrophoresis on cellulose acetate, using the Beckman Microzone electrophoretic unit. Several serum samples were also employed by the salt fractionation method. The results were comparable in all species, as shown in the following table:

| Animal | | Globulin Concentration gm. percent | | |
|---|---|---|---|---|
| | | Described Method | Electrophoresis | Salt Fractionation |
| Canine | 1 | 3.4 | 3.5 | 3.6 |
| | 2 | 3.9 | 3.8 | 4.0 |
| | 3 | 4.4 | 4.5 | 4.7 |
| Ovine | 1 | 3.4 | 3.3 | — |
| | 2 | 4.0 | 3.9 | — |
| | 3 | 3.9 | 4.0 | — |
| Bovine | 1 | 4.4 | 4.4 | |
| | 2 | 3.8 | 3.7 | |
| | 3 | 4.3 | 4.1 | |
| Feline | 1 | 3.2 | 3.4 | |
| | 2 | 3.2 | 3.2 | |
| | 3 | 2.9 | 2.9 | |
| Equine | 1 | 3.3 | 3.4 | |
| | 2 | 4.9 | 4.7 | |
| | 3 | 3.6 | 3.5 | |

EXAMPLE VI

In order to measure the comparative interference by albumin on the determination of globulin, several albumin solutions were reacted with the globulin reagent described in this disclosure and also with the reagents described by Goldenberg et al and Neeley et al. Much lower interference was observed using the reagent described in the disclosure as shown in the following table:

| Sample | Albumin Conc. by Biuret Reaction gm/dl | Globulin Equivalent By | | | | | |
|---|---|---|---|---|---|---|---|
| | | Described Method | | Goldenberg Method | | Neeley Method | |
| | | gm/dl | % | gm/dl | % | gm/dl | % |
| 1 | 17.0 | 1.3 | 7.6 | 4.2 | 25.0 | 4.0 | 24 |
| 2 | 8.2 | 0.58 | 7.0 | 2.2 | 26.8 | 2.1 | 26 |
| 3 | 4.6 | 0.25 | 5.0 | 1.1 | 23.9 | 1.2 | 26 |
| 4 | 2.8 | 0.12 | 4.3 | 0.56 | 20.0 | 0.67 | 24 |

EXAMPLE VII

The reagent for globulin determination as described under Example I (a) was stored at room temperature and at 37° C. It was used for the determination of globulin concentration of a pooled serum sample, preserved in a freeze-dried condition. No signs of deterioration of the reagent were found during a test period of six months at either temperature.

EXAMPLE VIII

The reagent described in the disclosure was reacted with the following solutions in triplicate in essentially the same procedure used for globulin determination:
1. Cholesterol solution 250 mg/dl
2. Normal pooled serum
3. The same serum with added cholesterol at the rate of 250 mg/dl. Their absorbances were read against the reagent blank. No color was produced by cholesterol as found from the results shown below:

| Sample | Absorbance Reading | | |
|---|---|---|---|
| | I | II | III |
| Cholesterol 250 mg/dl | 0.00 | 0.00 | 0.00 |
| Serum (without added cholesterol) | 0.33 | 0.32 | 0.32 |
| Same Serum with added cholesterol | 0.33 | 0.32 | 0.31 |

What is claimed is:

1. A composition useful for the determination of serum globulin comprising a photometrically reactive quantity of ethyl acetate and a catalytic quantity of ferric ion in a mixture of sulfuric acid and acetic acid and a sufficient volume of water to prevent said mixture from reacting with serum cholesterol.

2. The composition of claim 1, including serum.

3. The composition of claim 1, wherein the ferric ion is in the form of ferric perchlorate.

4. The composition of claim 1, wherein the volume of water is at least 15% v/v.

5. A composition useful for the determination of serum globulin comprising at least 10% v/v ethyl acetate, at least 0.01% w/v ferric perchlorate, at least 5% v/v sulfuric acid, not more than 70% v/v acetic acid and at least 15% v/v water.

6. The composition of claim 4, wherein the volume of acetic acid is about 32% v/v and the volume of water is about 36%.

7. A method useful for the determination of serum globulin comprising:
 a. mixing a minor amount of serum containing globulin with a reagent comprising ethyl acetate, ferric ion, sulfuric acid, acetic acid and at least 15% v/v water; and b. heating the mixture to a temperature from about 85° C. to about 100° C. for a period of from about 5 minutes to about 25 minutes.

8. A method for the determination of serum globulin comprising:
 a. mixing a minor amount of serum containing globulin with a reagent comprising ethyl acetate, ferric ion, sulfuric acid, acetic acid and at least 15% v/v water; and
 b. heating the mixture to a temperature from about 85° C. to about 100° C. for a period of from about 5 minutes to about 25 minutes; and
 c. determining the concentration of globulin by photometrically measuring color absorbance and comparing the reading against a calibration curve or the absorbance of a standard sample with known globulin concentrations.

9. The method of claim 7, wherein the ferric ion is in the form of ferric perchlorate.

* * * * *

UNITED STATES PATENT AND TRADEMARK OFFICE
CERTIFICATE OF CORRECTION

PATENT NO. : 4,116,633
DATED : September 26, 1978
INVENTOR(S) : Abdus Salam Mia

It is certified that error appears in the above-identified patent and that said Letters Patent are hereby corrected as shown below:

In Column 1, line 20, "by dilution of dialysis" should read
--- by dilution or dialysis---
In Column 3, line 30, "85°C. for a period" should read
---85°C. to 100°C. for a period---
In Column 4, line 12, "100 Milligrams" should read
---100 milligrams---

Signed and Sealed this

Thirteenth Day of February 1979

[SEAL]

Attest:

RUTH C. MASON
Attesting Officer

DONALD W. BANNER
Commissioner of Patents and Trademarks